(12) United States Patent
Kobayashi (10) Patent No.: US 12,239,334 B2
(45) Date of Patent: Mar. 4, 2025

(54) BASKET-TYPE TREATMENT TOOL FOR ENDOSCOPE

(71) Applicant: Makoto Kobayashi, Yokkaichi (JP)

(72) Inventor: Makoto Kobayashi, Yokkaichi (JP)

(*) Notice: Subject to any disclaimer, the term of this patent is extended or adjusted under 35 U.S.C. 154(b) by 532 days.

(21) Appl. No.: 17/609,048

(22) PCT Filed: Jun. 6, 2019

(86) PCT No.: PCT/JP2019/022537
§ 371 (c)(1),
(2) Date: Nov. 5, 2021

(87) PCT Pub. No.: WO2020/245978
PCT Pub. Date: Dec. 10, 2020

(65) Prior Publication Data
US 2022/0226007 A1     Jul. 21, 2022

(51) Int. Cl.
*A61B 17/221*     (2006.01)

(52) U.S. Cl.
CPC .... *A61B 17/221* (2013.01); *A61B 2017/2215* (2013.01); *A61B 2017/2217* (2013.01)

(58) Field of Classification Search
CPC ............ A61B 17/221; A61B 17/22031; A61B 2017/00296; A61B 2017/00862; A61B 2017/00867; A61B 2017/2212; A61B 2017/2215; A61B 2017/2217; A61B 2017/22034; A61B 2017/22035; A61B 2017/22038; A61B 1/307; A61B 17/32056
USPC .................................................. 606/127, 128
See application file for complete search history.

(56) References Cited

U.S. PATENT DOCUMENTS

| | | | |
|---|---|---|---|
| 5,059,199 A * | 10/1991 | Okada | A61B 17/221 606/127 |
| 6,585,734 B2 * | 7/2003 | Levinson | A61B 18/14 606/113 |
| 7,101,379 B2 | 9/2006 | Gregory, Jr. et al. | |
| 8,617,177 B2 | 12/2013 | Uhlein et al. | |
| 10,231,746 B1 | 3/2019 | Dostal et al. | |

(Continued)

FOREIGN PATENT DOCUMENTS

| | | |
|---|---|---|
| JP | 2000041987 A | 2/2000 |
| JP | 2002253557 A | 9/2002 |

(Continued)

OTHER PUBLICATIONS

Second Office Action cited in Korean Patent Appln. 10-2022-7000176 issued on Dec. 8, 2023.

(Continued)

*Primary Examiner* — Kankindi Rwego
(74) *Attorney, Agent, or Firm* — BACON&THOMAS,PLLC (57) ABSTRACT

To provide a basket-type treatment instrument for an endoscope such that wires constituting a basket are not liable to be damaged. A basket-type treatment instrument 1 for an endoscope having a basket part 40 formed such that a plurality of basket wires 41, 42 elastically expand or contract radially, wherein folded-back parts 41a, 42a formed by folding back substantially center portions of the basket wires 41, 42 are hooked to a substantially cylindrical first rib 6b fixed in a perpendicular direction to the cylinder axis of a distal tip 6, whereby the distal tip 6 retains the distal sides of the basket wires 41, 42 together.

7 Claims, 7 Drawing Sheets

(56) References Cited

U.S. PATENT DOCUMENTS

| 2003/0088254 | A1 | 5/2003 | Fanklin et al. |
| 2011/0066158 | A1 | 3/2011 | Teague et al. |
| 2011/0112547 | A1 | 5/2011 | Uihlein et al. |

FOREIGN PATENT DOCUMENTS

| JP | 3132410 U | 6/2007 |
| JP | 2011516126 A | 5/2011 |
| JP | 2018191986 A | 12/2018 |
| WO | WO2019039011 A1 | 2/2019 |

OTHER PUBLICATIONS

European Extended Search Report corresponding to European Patent Appln. No. 19931834.6 issued Jan. 5, 2023.

* cited by examiner

BASKET-TYPE TREATMENT TOOL FOR ENDOSCOPE

TECHNICAL FIELD

The present invention relates to a basket-type treatment tool for an endoscope inserted into a body cavity and provided with a treatment unit which pinches and crushes a foreign substance such as a stone within the body cavity by a basket constituted by a plurality of elastic wires, and more particularly to a basket-type treatment tool for an endoscope in which the wires constructing the basket is hard to be damaged.

BACKGROUND ART

In general, a doctor uses a basket-type treatment tool for an endoscope having a basket unit which can project and set with respect to an elongated flexible sheath and is expandable and contractable like a basket, for recovering and crushing the foreign substance such as the stone within the body cavity. The basket-type treatment tool for the endoscope is adapted to be inserted into an endoscope channel in a state in which a basket unit is housed in a flexible sheath so as to be moved close to the foreign substance such as the stone within the body cavity, make the basket unit protrude away from a distal end of the flexible sheath, introduce the stone in the basket unit, contract the basket unit by pulling an operation wire connected to the basket unit, and pulverize or hold and draw the stone.

The basket unit corresponding to the treatment unit of the basket-type treatment tool for the endoscope is formed by bringing together distal ends and proximal ends of a plurality of basket wires so that the basket wires elastically contract and expand at intervals. Bringing together and retaining the distal ends of the basket wires is generally performed by bringing together with a tip and jointing by means of welding, silver brazing or adhesive agent or caulking.

As a literature describing a basket-type treatment tool for an endoscope, for example, the following patent literature 1 is listed up.

A technique described in the patent literature 1 is adapted to form a wire constructing a basket unit as a flattened wire and apply a strong directionality in a vertical direction to a flattened surface when the basket unit expands and contracts, thereby making the wire harder to be affected by an external force of a mucosal fluid attached to the basket wire when expanding and contracting and facilitating capture of the stone.

Further, as a literature describing a basket-type treatment tool for an endoscope in which distal ends of a plurality of basket wires are retained to a tip without welding, for example, the following patent literature 2 is listed up.

A technique described in the patent literature 2 can bind a plurality of elastic wires in a desired correct positional relationship at distal ends thereof by firmly fixing four metal short tubes as distal end tips and inserting two sets of U-shaped bent-back basket wires into the short tubes one by one near the bent-back portion, thereby inflating the basket unit to an expected shape.

CITATION LIST

Patent Literature

Patent Literature 1: Japanese Patent Unexamined Publication No. 2002-253557

Patent Literature 2: Japanese Patent Unexamined Publication No. 2000-41987

SUMMARY OF INVENTION

Technical Problem

However, in a basket-type treatment tool for an endoscope described in the patent literature 1, a wire constructing a basket is inserted into a distal end binding pipe (a distal end tip) in a distal end thereof and is joined by silver brazing. Therefore, deterioration of the wire is caused by heat transmission of the high-temperature (about 600° C. to 970° C.) to the wire when joining, and there is a problem that the wire may be damaged by a force applied to the distal end portion when crushing the stone.

The conventional basket-type treatment tool for the endoscope which is joined by laser welding or soldering has such a problem that the high-temperature heat is transmitted to the wire in the same manner as mentioned above, and has such a problem that the wire is damaged due to deterioration of an adhesive agent when the adhesive agent is used. Further, the conventional basket-type treatment tool for the endoscope in which the wires are brought together by a tip is not affected by the temperature applied to the wire, however, is hard to set a caulking force, and has such a problem that the wire is injured by an external pressure and is damaged.

Further, in a basket-type treatment tool for an endoscope described in the patent literature 2, it is necessary to insert four small-diameter soft basket wires into four short tubes respectively from a distal end direction thereof, thereby making it hard to manufacture the basket-type treatment tool for the endoscope. Further, an entire outer diameter of the tip is enlarged for disposing the short tubes in parallel, thereby generating a problem that the tip is out of a field of view of the endoscope.

Taking into consideration the above-described problems, an object of the present invention is to provide a basket-type treatment tool for an endoscope which is hard to be damaged in a wire constructing a basket and can be easily manufactured.

Solution to Problem

In order to achieve the object mentioned above, according to a first aspect of the present invention, there is provided a basket-type treatment tool for an endoscope comprising an elongated cylindrical flexible sheath, an operation wire which is inserted into a cylinder of the flexible sheath and is movable forward and backward in an axial direction within the cylinder by being operated to be pushed and pulled, a basket unit which is provided in a distal end of the operation wire and is formed in such a manner that a plurality of basket wires are elastically contracted or expanded, a distal end tip which has an inner diameter portion extending like a cylinder and brings together distal end sides of the plurality of basket wires to retain, a proximal end tip which brings together proximal end sides of the plurality of basket wires to retain, a distal end metal fitting which is attached to the distal end of the flexible sheathe and inserts the operation wire with the basket unit thereto, and an operation unit for operating the operation wire to move forward and backward, wherein the distal end tip puts a turned-back portion formed by turning back an approximately center portion of the basket wire on an approximately columnar first rib fixed in a perpendicular direction to a tube axis of the distal end tip to retain, in which a direction toward the distal end tip is called as a distal end side, and a direction toward the operation unit is called as a proximal end side.

Further, according to a second aspect of the present invention, a groove is formed in the perpendicular direction to the tube axis in a distal end of the distal end tip, and the first rib is fixed to the groove, in the basket-type treatment tool for the endoscope according to the first aspect.

Further, according to a third aspect of the present invention, the inner diameter portion of the distal end tip has a small inner diameter area having a predetermined inner diameter for bringing together the basket wires to retain, and a large inner diameter area positioned closer to the proximal end side than the small inner diameter area, having a greater inner diameter than the small inner diameter area and allowing the basket wires to be movable in an inner portion thereof, in an axial direction, in the basket-type treatment tool for the endoscope according to the first aspect. According to a fourth aspect of the present invention, the inner diameter portion of the distal end tip has a small inner diameter area having a predetermined inner diameter for bringing together the basket wires to retain, and a large inner diameter area positioned closer to the proximal end side than the small inner diameter area, having a greater inner diameter than the small inner diameter area and allowing the basket wires to be movable in an inner portion thereof, in an axial direction, in the basket-type treatment tool for the endoscope according to the second aspect.

Further, according to a fifth aspect of the present invention, the basket unit is constructed by two basket wires, an approximately columnar second rib is fixed to a proximal end side of the distal end tip, the turned-back portion of one basket wire in the basket wires is put on the first rib, and the turned-back portion of the other basket wire is put on the second rib, in the basket-type treatment tool for the endoscope according to the first aspect. According to a sixth aspect of the present invention, the basket unit is constructed by two basket wires, an approximately columnar second rib is fixed to a proximal end side of the distal end tip, the turned-back portion of one basket wire in the basket wires is put on the first rib, and the turned-back portion of the other basket wire is put on the second rib, in the basket-type treatment tool for the endoscope according to the second aspect. According to a seventh aspect of the present invention, the basket unit is constructed by two basket wires, an approximately columnar second rib is fixed to a proximal end side of the distal end tip, the turned-back portion of one basket wire in the basket wires is put on the first rib, and the turned-back portion of the other basket wire is put on the second rib, in the basket-type treatment tool for the endoscope according to the third aspect. According to an eighth aspect of the present invention, the basket unit is constructed by two basket wires, an approximately columnar second rib is fixed to a proximal end side of the distal end tip, the turned-back portion of one basket wire in the basket wires is put on the first rib, and the turned-back portion of the other basket wire is put on the second rib, in the basket-type treatment tool for the endoscope according to the fourth aspect.

Further, according to a ninth aspect of the present invention, the second rib is fixed to the large inner diameter area in the basket-type treatment tool for the endoscope according to the seventh aspect. According to a tenth aspect of the present invention, the second rib is fixed to the large inner diameter area in the basket-type treatment tool for the endoscope according to the eighth aspect.

Effect of Invention

The treatment tool for the endoscope according to the present invention can retain the distal end of the basket wire to the distal end tip without caulking by putting the turned-back portion formed by turning back the approximately center portion of the basket wire on the approximately columnar first rib fixed in the perpendicular direction to the tube axis of the distal end top to retain. Therefore, the basket wire is hard to be damaged and the treatment tool for the endoscope can be easily manufactured.

DESCRIPTION OF EMBODIMENTS

A description will be in detail given below of an embodiment of a basket-type treatment tool for an endoscope according to the present invention with reference to the accompanying drawings. First of all, a description will be given of an overall structure of the basket-type treatment tool for the endoscope according to the embodiment of the present invention.

Embodiment 1

[Overall Structure]

Figure 1:
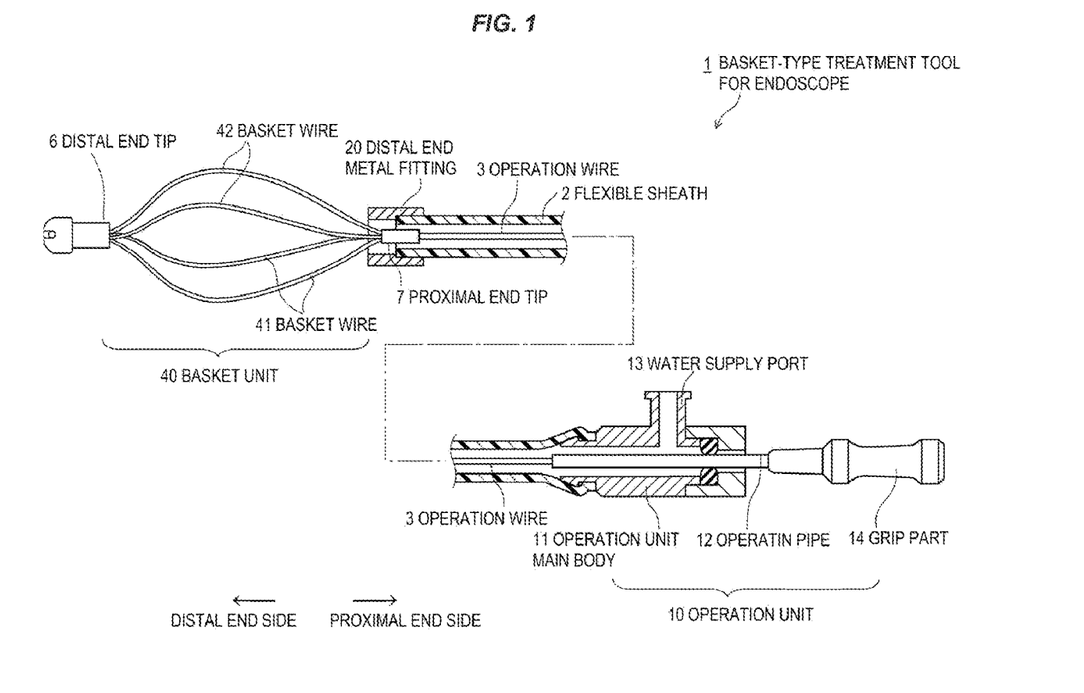
FIG. 1 is a view showing an overall configuration of a basket-type treatment tool for an endoscope according to an embodiment of the present invention.

As shown in FIG. 1, a basket-type treatment tool for an endoscope according to the present embodiment is provided with an elongated flexible sheath 2 which has an operation unit 10 attached to a proximal end thereof and is made of a resin or a coil, an operation wire 3 which is inserted into the flexible sheath 2 so as to be movable forward and backward, a cylindrical distal end metal fitting 20 which is arranged in a distal end of the flexible sheath 2 and is made of a hard metal material, and a foreign substance crushing basket unit 40 which is coupled to a distal end of the operation wire 3 and serves as a treatment unit capable of projecting and setting with respect to the flexible sheath 2 by pushing the operation wire 3 to the distal end side or pulling the operation wire 3 to the proximal end side on the basis of an operation of the operation unit 10.

In the present embodiment, a direction toward the operation unit 10 which is right in FIG. 1 is called as the proximal end side, and a direction toward the distal end tip 6 which is left in FIG. 1 is called as the distal end side.

The operation unit 10 is provided with a grip part 14 which is attached to the proximal end of the operation wire 3 via an operation pipe 12, and an operation unit body 11 through which the operation pipe 12 of the grip part 14 attached to the operation wire 3 passes, to which a water supply port 13 is opened, and which projects and sets the basket unit 40 in the distal end of the operation wire 3 with respect to the flexible sheath 2 by moving forward and backward the grip part 14. The water supply port 13 is communicated with a space in the cylinder of the operation unit body 11 in an inner end portion thereof, and is configured to attach an injection (not shown) thereto and allow a drug solution to be fed into the flexible sheath 2.

The basket unit 40 is constructed by a plurality of basket wires 41 and 42 obtained by turning back an elongated linear twisted wire approximately at the center and forming a distal end in the turned-back portion (in the present embodiment, the basket unit 40 is constituted by four turned-back portions obtained by turning back two basket wires), the distal end tip 6 which brings together the turned-back distal ends of the basket wires 41 and 42 to retain and is a feature of the present embodiment, and a proximal end tip 7 which brings together the proximal ends of the basket wires 41 and 42 to fix. The treatment unit is formed in such a manner that a plurality of basket wires 41 and 42 elastically contract and expand at intervals.

The basket unit 40 is self-biased in such a manner that each of the basket wires 41 and 42 is curved and inflated outward, the basket wires 41 and 42 are arranged in a stereoscopically linear symmetrical relationship around a center axis of the basket unit 40, and the basket unit 40 is configured to be contracted within the flexible sheath 2 and be inflated and expanded by a self-biasing force in a protruding state from the distal end of the flexible sheath 2 so as to form an approximately basket shape.

[Description of Overall Motion]

The basket-type treatment tool for the endoscope according to the present embodiment constructed as described above is inserted into a body cavity of a patient through a channel of an endoscope device previously inserted into the body cavity of the patient and is used for crushing a stone to be recovered. An example of this operation will be described with reference to FIGS. 8A to 8D.

Figures 8A, 8B:
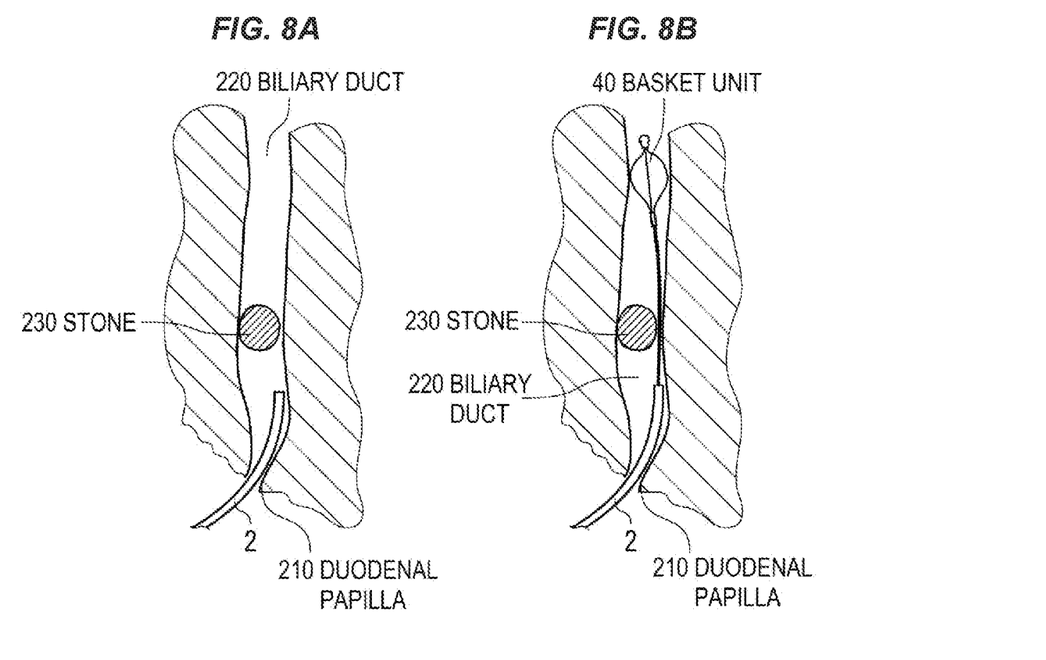
FIGS. 8A to 8D are views for describing an operation example of a basket-type treatment tool for an endoscope to which the present invention is applied.
Figures 8C, 8D:
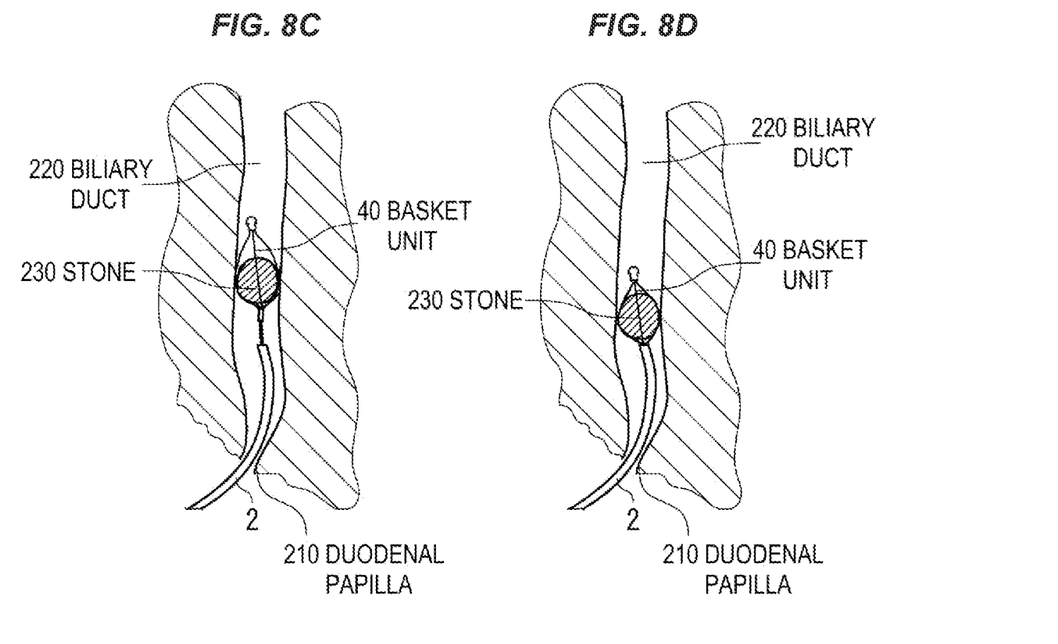

The operation with the basket-type treatment tool for the endoscope is performed by a step of pulling the operation wire and inserting the flexible sheath 2 in a state in which the basket unit in the distal end is drawn into an inner portion and is contracted into a biliary duct 220 within a duodenal papilla 210, by a doctor, as shown in FIG. 8A, a next step of pushing out the operation wire, opening the basket unit 40 from the distal end of the flexible sheath 2 and moving to a far position from a stone 230, as shown in FIG. 8B, a next step of protruding the operation wire, drawing the operation wire into the flexible sheath 2 and trapping the stone 230 into a gap of the basket unit 40, as shown in FIG. 8C, and a further step of further drawing the basket unit 40 into the flexible sheath 2, pinching between the distal end metal fitting in the distal end of the flexible sheath 2 and the basket unit 40 and constricting the stone 230, thereby crushing the stone 230, as shown in FIG. 8D.

[Structure of Distal End Tip]

Figure 5A:
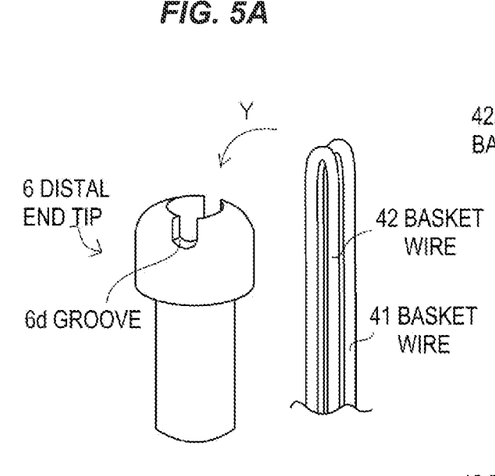
FIGS. 5A to 5D are views for describing attachment of a basket wire to the distal end tip according to the embodiment 1 of the present invention.
Figure 5B:
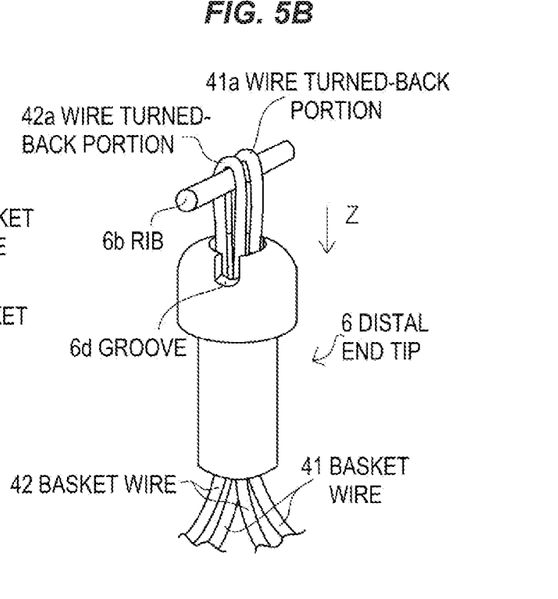
Figure 5C:
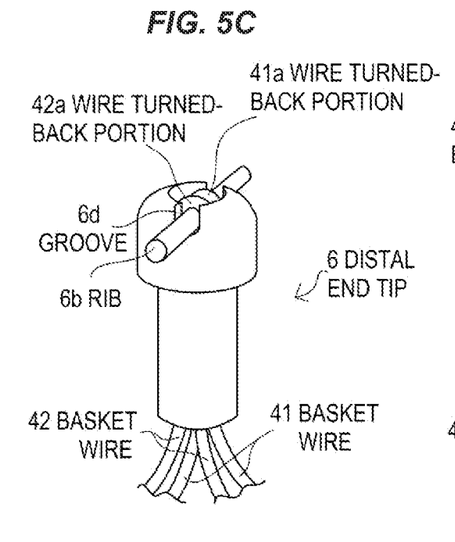
Figure 5D:
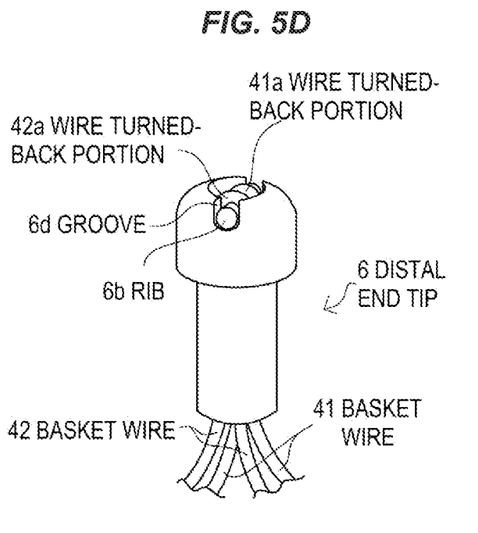

The distal end tip 6 corresponding to the feature of the present embodiment has been conventionally constructed, for example, by inserting the distal ends of four basket wires and fixing them by caulking or welding. In order to reduce the wire damage and easily manufacture, the distal end tip 6 of the present embodiment is constructed by inserting two basket wires 41 and 42 into an opening portion in a distal end of the distal end tip 6 in a state of being turned back as shown in FIG. 5A, putting a rib 6b on turned-back portions 41a and 42a of the basket wires 41 and 42 as shown in FIG. 5B, cutting both ends of the rib 6b and pressing the basket wires 41 and 42 into the distal end tip as shown in FIGS. 5C and 5D, details of which will be mentioned later. Next, a detailed structure thereof will be described.

A description will be given of the distal end tip 6 corresponding to the feature of the present embodiment with reference to FIGS. 2A to 4B.

Figure 2A:
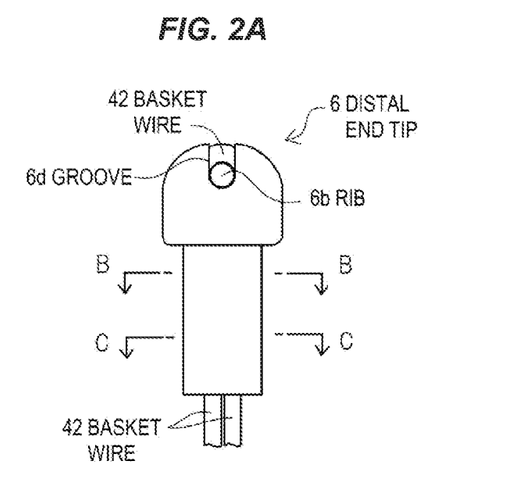
FIGS. 2A to 2E are views showing a distal end tip of a basket-type treatment tool for an endoscope according to an embodiment 1 of the present invention.
Figure 2B:
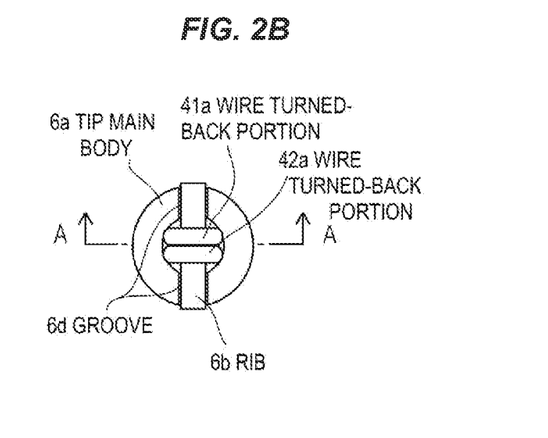
Figure 2C:
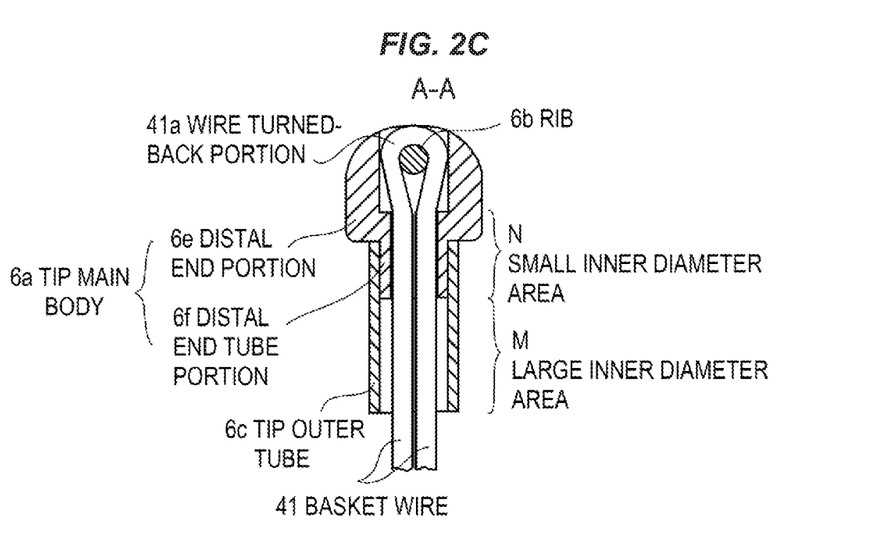
Figure 2D:
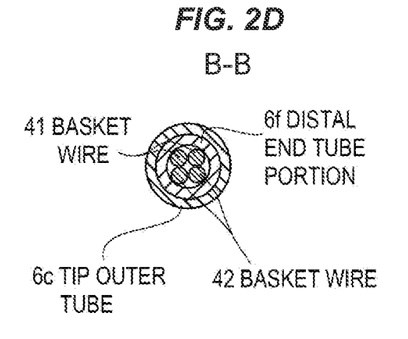
Figure 2E:
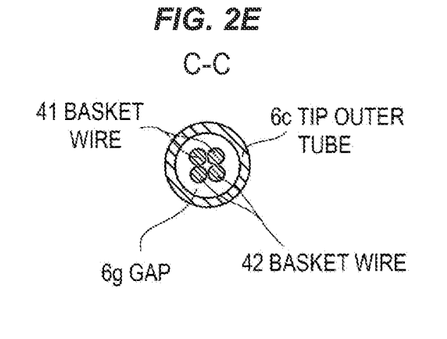

FIG. 2A shows an outer appearance diagram of the distal end tip 6, FIG. 2B shows a view of FIG. 2A as seen from the distal end side (an upward direction of FIG. 2A), FIG. 2C shows a cross sectional view along a line A-A in FIG. 2B, FIG. 2D shows a cross sectional view along a line B-B in FIG. 2A, and FIG. 2E shows a cross sectional view along a line C-C in FIG. 2A, in which the basket wires 41 and 42 are shown in a state in which they are not expanded like a basket, but are closed.

As shown in FIGS. 2A and 2C, the distal end tip 6 is constructed by a distal end portion 6e which is formed into an approximately semispherical shape in a distal end side thereof so as to prevent an inner wall of the body cavity from being injured, a hollow tip main body 6a which is formed in a proximal end side thereof into a tubular shape which can be fitted to a tip outer tube 6c mentioned later, and includes a distal end tube portion 6f having a small inner diameter area N, and a tubular tip outer tube 6c which is fitted to an outer periphery of the distal end tube portion 6f of the tip main body 6a and is fixed by laser welding, and has a tubular inner diameter portion with level difference as a whole.

As shown in FIG. 2C, the inner diameter portion has the small inner diameter area N having a predetermined inner diameter for bringing together the basket wires 41 and 42 mentioned later to retain, and a large inner diameter area M which is positioned closer to the proximal end side than the small inner diameter area, has a larger diameter than the small inner diameter area N, and allows the basket wires 41 and 42 to be movable in an inner portion thereof.

The distal end tip 6 is provided in the distal end of the distal end portion 6e of the tip main body 6a with grooves 6d and 6d at symmetrical positions at the center of the perpendicular direction to the tube axis, and an axial length (groove depth) of the grooves 6d and 6d is desirably set to the same level as a length obtained by adding a diameter of the basket wire and a diameter of a rib 6b mentioned later, as shown in FIGS. 2A to 2C.

Further, an approximately columnar first rib 6b is fitted and fixed to the grooves 6d and 6d. The respective wire turned-back portions 41a and 42a of the basket wires 41 and 42 are put on the first rib 6b. A length of the rib 6b is preferably set to about the same length as the diameter of the distal end portion 6e of the distal end tip 6 since the protruding portion of the distal end tip 6 may injure the inner wall of the body cavity when being fixed to the groove 6d if the outward protruding portion of the distal end tip 6 is long.

Further, a part closer to the proximal end side than the wire turned-back portion 41a and the wire turned-back portion 42a is pressed into the distal end tube portion 6f, so that outer peripheries of the basket wires 41 and 42 are partly retained respectively in a state of being in contact with the distal end tube portion 6f, as shown in FIG. 2D.

In the meantime, the tip outer tube 6c forms an inner diameter fitting to an outer periphery of the distal end tube portion 6f. As shown in FIGS. 2C to 2E, a large inner diameter area having a gap 6g corresponding to a thickness of the distal end tube portion 6f is positioned between the basket wires 41 and 42 and an inner periphery of the tip outer tube 6c.

In the present embodiment, the basket wires 41 and 42 are structured such that the elongated linear twisted wire is turned back approximately at the center portion and the turned-back portion forms the distal end of the basket wire, thereby forming a pair by two basket wires 41 and 41 and a pair by two basket wires 42 and 42 in FIG. 1. However, the structure is not limited to this, but the basket may be constructed by three pairs, each pair being constituted by two basket wires.

[Dimension]

Figure 4A:
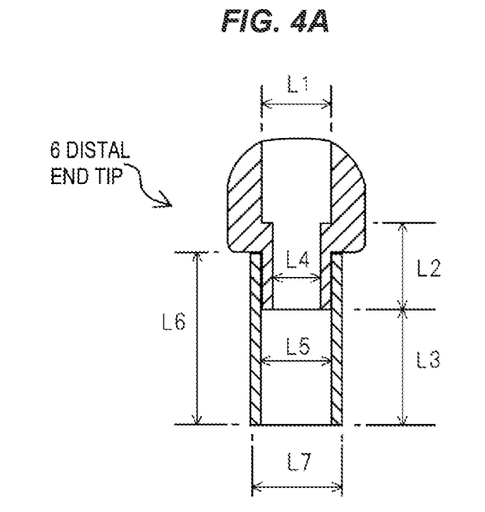
FIGS. 4A and 4B are views for describing a dimension of the distal end tip according to the embodiment 1 of the present invention.
Figure 4B:
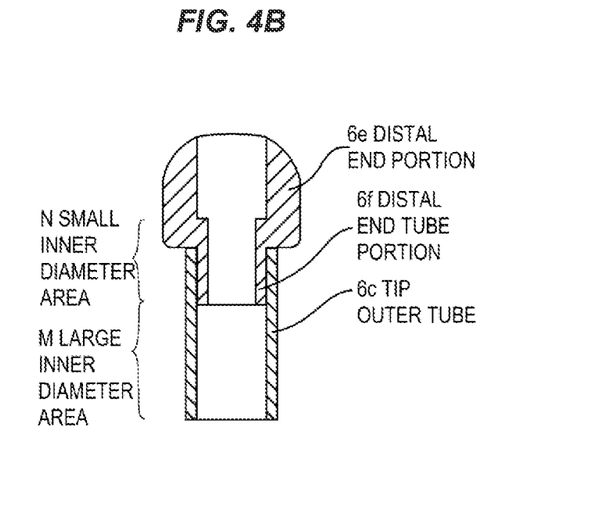

Next, a dimension of the distal end tip 6 will be described with reference to FIGS. 4A and 4B (in which the basket wires 41 and 42 and the rib 6b are not shown). A specific example of dimensions of the respective members is an example in a case where a diameter of the basket wires 41 and 42 is set to 0.35 mm and two pairs of basket wires, that is, four basket wires are employed, however, the dimension is not limited to this.

An inner diameter L4 of the small inner diameter area N in the distal end tube portion 6f of the distal end tip 6 is a diameter which can press a part closer to the proximal end side than each of the wire turned-back portions 41a and 42a of the basket wires 41 and 42 thereinto and can retain a part of the outer peripheries of the basket wires 41 and 42 in an internal contact manner, as mentioned above, for example, about 0.86 mm. Further, a length L2 of the small inner diameter area N is about 1.5 mm, for example.

An inner diameter L1 of the distal end side of the distal end portion 6e is larger than the inner diameter L4 of the distal end tube portion 6f for housing each of the turned-back portions 41a and 42a of the basket wires 41 and 42 and the rib 6b, for example, about 1.2 mm.

An inner diameter L5 of the tip outer tube 6c is approximately the same diameter as an outer diameter of the distal end tube portion 6f for fitting to the distal end tube portion 6f, for example, about 1.2 mm.

A length L3 of the large inner diameter area M of the tip outer tube 6c is required to be such a length that the basket wires 41 and 42 mentioned above are movable, and is necessarily at least about 1.5 times to 6 times of the inner diameter L5, for example, about 2 mm, and a length L6 of the tip outer tube 6c is about 3 mm, for example.

[Assembling Method]

Next, a description will be given of a method of attaching the basket wires 41 and 42 to the distal end tip 6 with reference to FIGS. 5A to 5D.

The assembling method first performs a step of inserting the proximal end sides of the basket wires 41 and 42 turned back approximately at the center portion of the elongated linear twisted wire from the distal end side of the distal end tip 6 toward the proximal end side (in a direction of an arrow Y in the drawing) as shown in FIG. 5A, next a step of passing the rib 6b through the gap of the turned-back portions 41a and 42a in a state in which each of the wire turned-back portions 41a and 42a of the basket wires 41 and 42 protrude out of the distal end tip 6 as shown in FIG. 5B, and a step of pressing the basket wires 41 and 42 toward the proximal end side of the distal end tip 6 (in a direction of an arrow Z in the drawing).

Next, the present assembling method performs a step of fitting the rib 6b to the groove 6d and fixing the rib 6b to the groove 6d by laser welding as shown in FIG. 5C, and a step of cutting the protruding portion of the rib 6b protruding out of the distal end tip 6 as shown in FIG. 5D.

According to the assembling method, in the distal end tip according to the present embodiment, the wire is not damaged by thermal welding, and the distal end tip can be easily manufactured since the wire is pressed into the distal end tip in a state in which two turned-back portions are put on the rib as the distal end.

In the present embodiment, there is shown the example in which the protruding portion is cut after the rib 6b is fixed to the groove 6d. However, the structure is not limited to this, but the length of the rib 6b may be cut to the length which does not protrude out of the distal end tip and the rib 6b may be fixed to the groove 6d.

Effect

As mentioned above, the basket-type treatment tool for the endoscope 1 shown in the present embodiment is configured to press the wire into the distal end tip in a state in which the turned-back portions 41a and 42a obtained by turning back two basket wires 41 and 42 are set as the distal end and put on the approximately columnar rib 6b as described above. The basket-type treatment tool for the endoscope 1 has the following effects.

The basket-type treatment tool for the endoscope 1 shown in the present embodiment can bring together the basket wires 41 and 42 with the distal end tip by putting each of the wire turned-back portions 41a and 42a of the basket wires 41 and 42 on the approximately columnar rib 6b and fixing the rib 6b to the groove 6d of the distal end tip 6 as described above without applying any heat of welding to each of the turned-back portions 41a and 42a of the basket wires 41 and 42, and is no danger of damage in the basket wire due to the heat. Further, in addition to this, in the present basket-type treatment tool for the endoscope 1, the basket wires 41 and 42 can be retained within the small inner diameter area N, since the basket wires 41 and 42 are pressed into the small inner diameter area N of the distal end tip.

Further, in the basket-type treatment tool for the endoscope 1 according to the present embodiment, the columnar outer periphery of the rib 6b smoothly comes into contact with the inner side of the wire turned-back portions 41a and 42a when the basket wires 41 and 42 are put, since the rib 6b is formed into the approximately columnar shape which has no angles. Therefore, the force applied to the wire turned-back portions 41a and 42a is dispersed in a case where the strong force is applied when crushing the stone, in comparison with the case of the angled shape, so that basket wires 41 and 42 are hard to be damaged.

Further, the present basket-type treatment tool for the endoscope 1 is a simple structure in which the rib 6b is fixed to the distal end tip 6 and the basket wire is put thereon. Thus, the present basket-type treatment tool for the endoscope 1 can be easily manufactured, and is in no danger of becoming too large in the outer diameter of the distal end tip to be out of the visual field of the endoscope.

Further, in the present basket-type treatment tool for the endoscope 1, the basket wires 41 and 42 move in an allowable range formed by the gap 6g when gripping the stone since the gap 6g is provided between the basket wires 41 and 42 and the tip outer tube 6c. Therefore, the basket-type treatment tool for the endoscope is hard to be incarcerated and the incarceration is easy to be cancelled even in a case where being incarcerated.

Figures 3A, 3B:
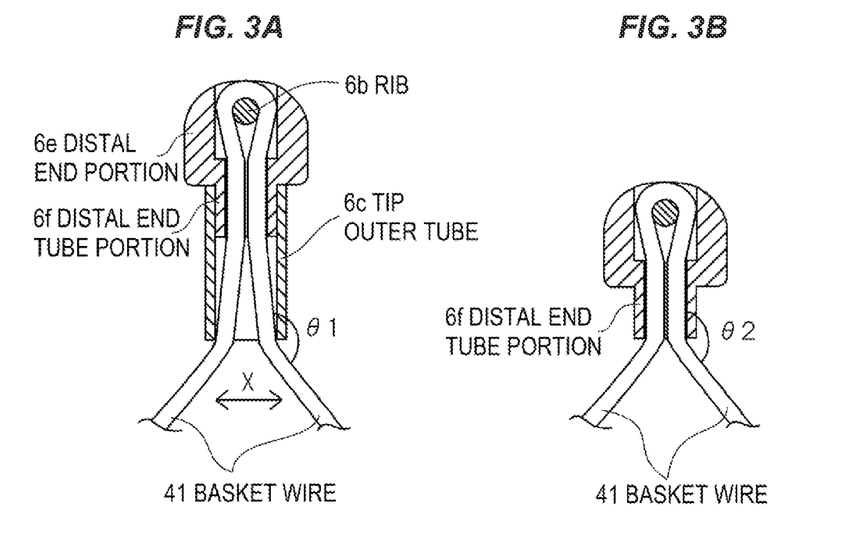
FIGS. 3A and 3B are views for describing a difference of the distal end tip of the basket-type treatment tool for the endoscope according to the embodiment 1 of the present invention from a conventional distal end tip.

More specifically, the basket-type treatment tool for the endoscope 1 according to the present embodiment is provided with the gap 6g with respect to the inner periphery of the tip outer tube 6c of the distal end tip 6 in a state in which the basket wires 41 and 42 are narrowed. Thus, as shown in FIG. 3A, even in a case where the basket wires 41 and 42 (42 is not shown) are expanded like a basket and the stone is stuck in the inner portion of the basket unit 40 and does not move, the basket wires 41 and 42 can move in the inner portion of the tip outer tube 6c in a direction of X (a direction in which the basket wires 41 and 42 is expanded like a basket and narrowed) by operating the operation wire 2 to push and pull. Therefore, the stone can be moved little by little and a gap is formed between the basket wires 41 and 42 and the stone gradually, thereby cancelling the incarceration.

Further, the basket wire 41 is folded at a small (acute) folding angle θ2 from the protruding position from the distal end tube portion 6f having no gap in a case where the tip outer tube 6c is not provided, as shown in FIG. 3B. On the contrary, in the basket-type treatment tool for the endoscope 1 according to the present embodiment, a folding angle θ1 from the protruding position from the tip outer tube 6c is greater (obtuse) as shown in FIG. 3A, thereby achieving an effect that the basket wire is less eaten into the stone and is hard to be incarcerated.

Embodiment 2

Next, a description will be given of an second embodiment 2 of the basket-type treatment tool for the endoscope 1 according to the present invention with reference to FIGS. 6A to 6D.

Figure 6A:
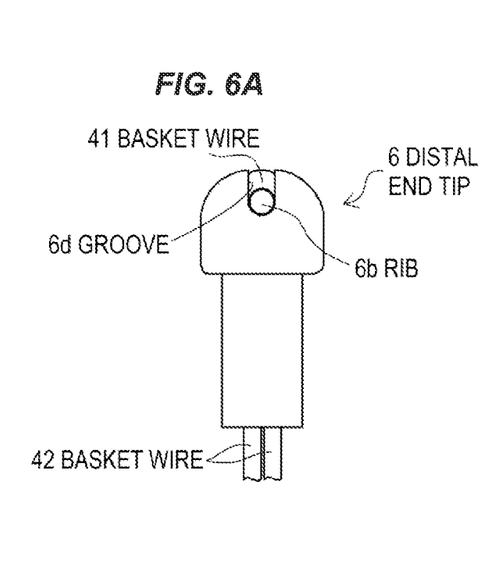
FIGS. 6A to 6D are views showing a distal end tip of a basket-type treatment tool for an endoscope according to an embodiment 2 of the present invention.
Figure 6B:
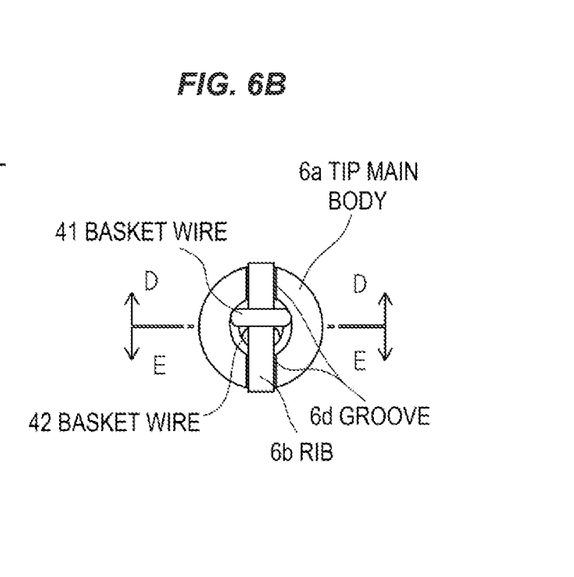
Figures 6C, 6D:
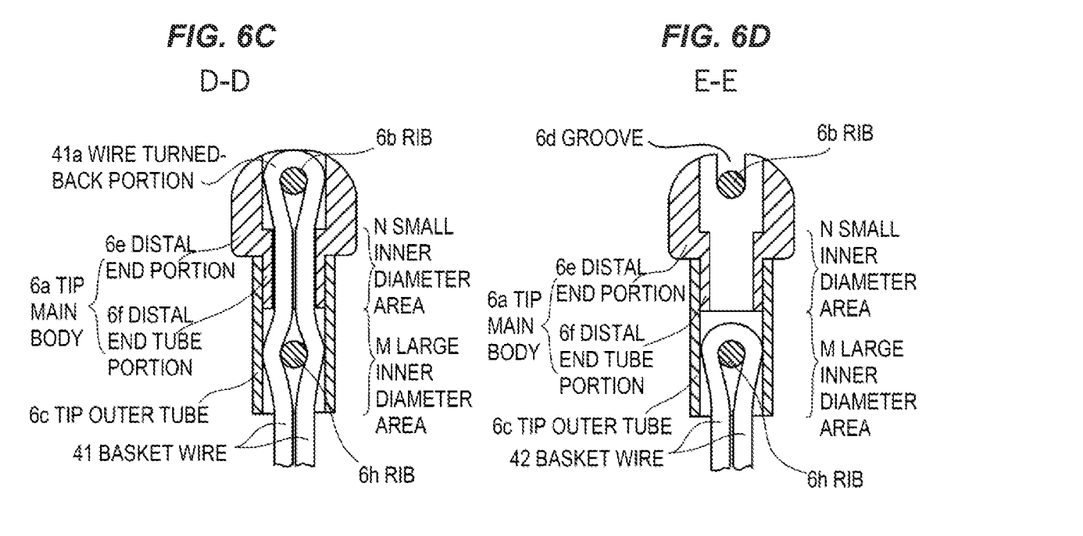

FIG. 6A shows an outer appearance diagram of a distal end tip 6, FIG. 6B shows a view of FIG. 6A as seen from a distal end side (an upward direction of FIG. 6A), FIG. 6C is a cross sectional view along a line D-D in FIG. 6B, and FIG. 6D shows a cross sectional view along a line E-E in FIG. 6B, in which basket wires 41 and 42 are shown in a state in which the basket wires 41 and 42 are not expanded like a basket, but are closed.

The other structures than the distal end tip are same as those of the embodiment 1 and a description thereof will be omitted.

In the embodiment mentioned above, there is shown the example in which the rib 6b putting each of the turned-back portions 41a and 42a of the basket wires 41 and 42 thereon is fixed to the groove 6d of the distal end tip 6. However, the structure is not limited to this, but the basket-type treatment tool for the endoscope 1 according to the embodiment 2 may be structured, for example, as shown in FIGS. 6A to 6D, such that two ribs are fixed to the distal end tip 6 and the basket wire is put on each of the ribs.

More specifically, in the basket-type treatment tool for the endoscope according to the embodiment 2, as shown in FIGS. 6A to 6D, a groove 6d is formed in a distal end portion 6e of the distal end tip in the same manner as the embodiment 1, a first rib 6b putting the turned-back portion 41a of the basket wire 41 thereon is fixed to the groove 6d, and an approximately columnar second rib 6h putting the turned-back portion 42a of the basket wire 42 thereon is fixed to a large inner diameter area M of a tip outer tube 6c. The rib 6h may be directly welded to an inner portion of the tip outer tube 6c by laser, or a groove may be formed in a proximal end of the tip outer tube 6c at the center in a perpendicular direction to the tube axis and the rib 6h may be fixed to the groove.

The basket wire 41 is arranged in the large inner diameter area M so as to avoid the rib 6h.

In the basket-type treatment tool for the endoscope according to the present embodiment, the approximately columnar rib 6b putting the wire turned-back portion 41a of the basket wire 41 thereon is fixed to the groove 6d of the distal end tip 6, and the approximately columnar rib 6h putting the turned-back portion 42a of the basket wire 42 thereon is fixed within the tip outer tube 6c, as described above. Thus, the basket wires 41 and 42 can be brought together by the distal end tip without applying any heat generated by welding to each of the turned-back portions 41a and 42a of the basket wires 41 and 42, and it is possible to prevent the basket wire from being damaged by the heat.

Further, in the present basket-type treatment tool for the endoscope, the columnar outer peripheries of the ribs 6b and 6h smoothly comes into contact with the inner side of the wire turned-back portions 41a and 42a when the basket wires 41 and 42 are put, since the ribs 6b and 6h are formed into the approximately columnar shape which has no angles. Therefore, the force applied to the wire turned-back portions 41a and 42a is dispersed in a case where the strong force is applied when crushing the stone, in comparison with the case of the angled shape, so that basket wires 41 and 42 are hard to be damaged.

Embodiment 3

Next, a description will be given of an embodiment 3 of the basket-type treatment tool for the endoscope 1 according to the present invention with reference to FIGS. 7A to 7C.

Figure 7A:
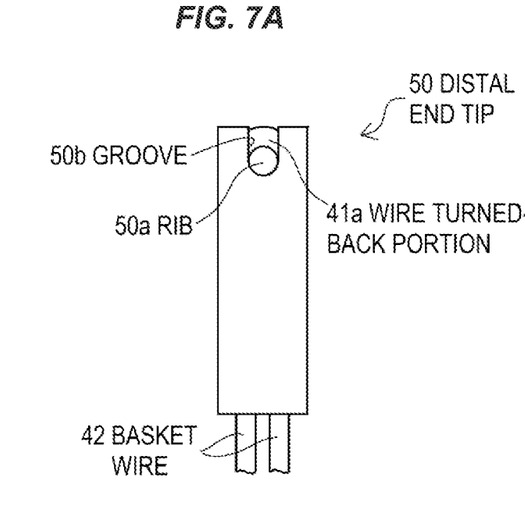
FIGS. 7A to 7C are views showing a distal end tip of a basket-type treatment tool for an endoscope according to an embodiment 3 of the present invention.
Figure 7B:
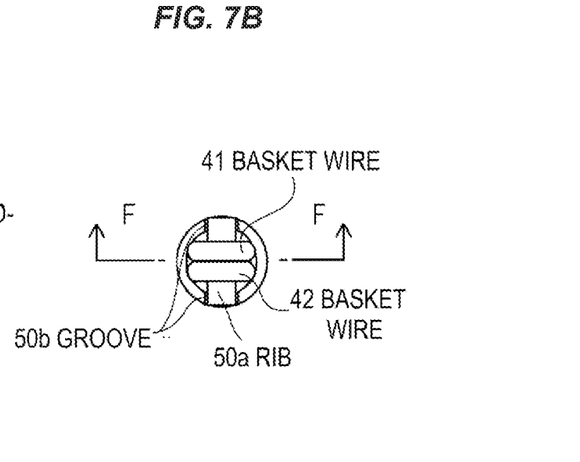
Figure 7C:
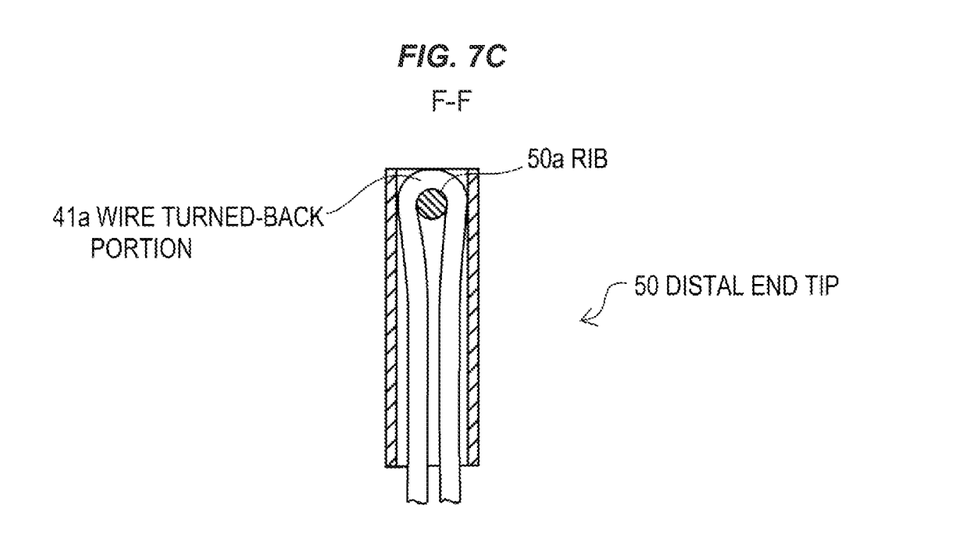

FIG. 7A shows an outer appearance diagram of a distal end tip 50, FIG. 7B shows a view of FIG. 7A as seen from a distal end side (in an upward direction of FIG. 7A), and FIG. 7C shows a cross sectional view along a line F-F in FIG. 7B, in which basket wires 41 and 42 are shown in a state in which they are not expanded like a basket, but are closed.

The other structures than the distal end tip are the same as those of the embodiment 1, and a description thereof will be accordingly omitted.

In the embodiment mentioned above, there is shown the example in which the distal end tip is constructed by assembling two members constituted by the tip main body and the tip outer tube. However, the structure is not limited to this, but the basket-type treatment tool for the endoscope according to the embodiment 3 may be structured such that the distal end tip 50 is formed into a tubular shape, grooves 50b and 50b are provided in a distal end thereof at the center in a perpendicular direction to a tube axis, and an approximately columnar rib 50a on which each of the wire turned-back portions 41a and 42a of the basket wires 41 and 42 is put, is fitted and fixed to the groove 50a and 50b.

In the basket-type treatment tool for the endoscope according to the present embodiment, the basket wires 41 and 42 can be brought together by the distal end tip without applying any heat by welding to each of the turned-back portions 41a and 42a of the basket wires 41 and 42 by fixing the approximately columnar rib 50a on which each of the wire turned-back portions 41a and 42a of the basket wires 41 and 42 is put to the groove 50b of the distal end tip 50, in the same manner as the embodiment mentioned above. Therefore, it is possible to prevent the basket wire from being damaged by the heat.

Further, in the present basket-type treatment tool for the endoscope, the outer periphery of the column of the rib 50*a* smoothly comes into contact with the inner side of the wire turned-back portions 41*a* and 42*a* when the basket wires 41 and 42 are put thereon since the rib 50*a* is formed into the approximately columnar shape which has no angles. Therefore, the force applied to the wire turned-back portions 41*a* and 42*a* is dispersed in a case where the strong force is applied when crushing the stone, in comparison with the case of the angled shape, so that basket wires 41 and 42 are hard to be damaged.

The rib on which each of the turned-back portions 41*a* and 42*a* of the basket wires 41 and 42 is put may be fixed at two positions constituted by the distal end side and the proximal end side by combining the present embodiment with the embodiment 2 mentioned above.

The invention claimed is:

1. A basket-type treatment tool for an endoscope, comprising:
   an elongated cylindrical flexible sheath;
   an operation wire inserted into a cylinder of the flexible sheath and movable forward and backward in an axial direction within the cylinder by pushing and pulling;
   a basket unit provided in a distal end of the operation wire and formed in such a manner that a plurality of basket wires are elastically contracted or expanded;
   a distal end tip having a cylindrical inner diameter portion and configured to retain distal end sides of the plurality of basket wires;
   a proximal end tip holding together to retain proximal end sides of the plurality of basket wires;
   a distal end metal fitting which is attached to a distal end of the flexible sheath and into which the operation wire with the basket unit is inserted; and
   an operation unit for operating the operation wire to move forward and backward,
   wherein the distal end tip puts a turned-back portion formed by turning back an approximately center portion of each respective basket wire on an approximately columnar first rib fixed in a perpendicular direction to a tube axis of the distal end tip to retain the respective basket wire in said distal end tip, in which a direction toward the distal end tip is called as a distal end side, and a direction toward the operation unit is called as a proximal end side, and
   wherein the inner diameter portion of the distal end tip has a small inner diameter area having a predetermined inner diameter for bringing together the basket wires to retain, and a large inner diameter area positioned closer to the proximal end side than the small inner diameter area, having a greater inner diameter than the small inner diameter area and allowing the basket wires to be movable in an inner portion thereof, in an axial direction.

2. The basket-type treatment tool for the endoscope according to claim 1, wherein a groove is formed in the perpendicular direction to the tube axis in a distal end of the distal end tip, and the first rib is fixed to the groove.

3. The basket-type treatment tool for the endoscope according to claim 2, wherein the basket unit is constructed by two basket wires, and
   wherein an approximately columnar second rib is fixed to a proximal end side of the distal end tip, the turned-back portion of one basket wire in the basket wires is put on the first rib, and the turned-back portion of the other basket wire is put on the second rib.

4. A basket-type treatment tool for an endoscope, comprising:
   an elongated cylindrical flexible sheath;
   an operation wire inserted into a cylinder of the flexible sheath and movable forward and backward in an axial direction within the cylinder by pushing and pulling;
   a basket unit provided in a distal end of the operation wire and formed in such a manner that a plurality of basket wires are elastically contracted or expanded;
   a distal end tip having a cylindrical inner diameter portion and configured to retain distal end sides of the plurality of basket wires;
   a proximal end tip holding together to retain proximal end sides of the plurality of basket wires;
   a distal end metal fitting which is attached to a distal end of the flexible sheath and into which the operation wire with the basket unit is inserted; and
   an operation unit for operating the operation wire to move forward and backward,
   wherein the distal end tip puts a turned-back portion formed by turning back an approximately center portion of each respective basket wire on an approximately columnar first rib fixed in a perpendicular direction to a tube axis of the distal end tip to retain the respective basket wire in said distal end tip, in which a direction toward the distal end tip is called as a distal end side, and a direction toward the operation unit is called as a proximal end side,
   wherein a groove is formed in the perpendicular direction to the tube axis in a distal end of the distal end tip, and the first rib is fixed to the groove, and
   wherein the inner diameter portion of the distal end tip has a small inner diameter area having a predetermined inner diameter for bringing together the basket wires to retain, and a large inner diameter area positioned closer to the proximal end side than the small inner diameter area, having a greater inner diameter than the small inner diameter area and allowing the basket wires to be movable in an inner portion thereof, in an axial direction.

5. The basket-type treatment tool for the endoscope according to claim 4, wherein the basket unit is constructed by two basket wires, and
   wherein an approximately columnar second rib is fixed to a proximal end side of the distal end tip, the turned-back portion of one basket wire in the basket wires is put on the first rib, and the turned-back portion of the other basket wire is put on the second rib.

6. The basket-type treatment tool for the endoscope according to claim 5, wherein the second rib is fixed to the large inner diameter area.

7. A basket-type treatment tool for an endoscope, comprising:
   an elongated cylindrical flexible sheath;
   an operation wire inserted into a cylinder of the flexible sheath and movable forward and backward in an axial direction within the cylinder by pushing and pulling;
   a basket unit provided in a distal end of the operation wire and formed in such a manner that a plurality of basket wires are elastically contracted or expanded;
   a distal end tip having a cylindrical inner diameter portion and configured to retain distal end sides of the plurality of basket wires;
   a proximal end tip holding together to retain proximal end sides of the plurality of basket wires;

a distal end metal fitting which is attached to a distal end of the flexible sheath and into which the operation wire with the basket unit is inserted; and an operation unit for operating the operation wire to move forward and backward, wherein the distal end tip puts a turned-back portion formed by turning back an approximately center portion of each respective basket wire on an approximately columnar first rib fixed in a perpendicular direction to a tube axis of the distal end tip to retain the respective basket wire in said distal end tip, in which a direction toward the distal end tip is called as a distal end side, and a direction toward the operation unit is called as a proximal end side, wherein the basket unit is constructed by two basket wires, and wherein an approximately columnar second rib is fixed to a proximal end side of the distal end tip, the turned-back portion of one basket wire in the basket wires is put on the first rib, and the turned-back portion of the other basket wire is put on the second rib.

* * * * *